(12) United States Patent
Dueva et al.

(10) Patent No.: US 8,465,729 B2
(45) Date of Patent: Jun. 18, 2013

(54) SUNSCREEN COMPOSITIONS WITH SPF ENHANCER

(75) Inventors: Olga V. Dueva, White Plains, NY (US); James P. Sanogueira, Suffern, NY (US)

(73) Assignee: Playtex Products, Inc., Westport, CT (US)

( * ) Notice: Subject to any disclaimer, the term of this patent is extended or adjusted under 35 U.S.C. 154(b) by 1103 days.

(21) Appl. No.: 11/099,123

(22) Filed: Apr. 5, 2005

(65) Prior Publication Data

US 2006/0008427 A1    Jan. 12, 2006

Related U.S. Application Data

(60) Provisional application No. 60/559,858, filed on Apr. 6, 2004.

(51) Int. Cl.
*A61K 8/00*    (2006.01)
*A61K 8/49*    (2006.01)

(52) U.S. Cl.
USPC ............................................ 424/59; 424/70.9

(58) Field of Classification Search
USPC .................................................. 424/59, 70.9
See application file for complete search history.

(56) References Cited

U.S. PATENT DOCUMENTS

| | | | |
|---|---|---|---|
| 5,773,611 A | 6/1998 | Zysman et al. | |
| 5,980,871 A * | 11/1999 | Lukenbach et al. | 424/59 |
| 6,630,163 B1 * | 10/2003 | Murad | 424/464 |
| 6,787,147 B1 * | 9/2004 | Huner et al. | 424/401 |
| 7,611,696 B2 * | 11/2009 | Berg-Schultz | 424/59 |
| 2004/0241254 A1 * | 12/2004 | Kopas et al. | 424/727 |

* cited by examiner

*Primary Examiner* — Lezah Roberts
*Assistant Examiner* — Nannette Holloman
(74) *Attorney, Agent, or Firm* — Ohlandt, Greeley, Ruggiero and Perle, L.L.P.

(57) ABSTRACT

The present invention provides a photo-protective composition that has a synergistic combination of at least one sunscreen agent and at least one carotenoid, which results in a composition with an increased SPF compared to a composition without the synergistic combination. Preferably, the composition also has at least one of the following additional components: emulsifier, emollient, skin-feel additive, moisturizing agent, film former/waterproofing agent, pH adjuster/chelating agent, preservative, or any combinations thereof.

12 Claims, No Drawings

SUNSCREEN COMPOSITIONS WITH SPF ENHANCER

RELATED APPLICATION

This patent application claims priority to Provisional Patent Application Ser. No. 60/559,858, filed on Apr. 6, 2004.

BACKGROUND OF THE INVENTION

1. Field of the Invention

The present invention relates to photo-protective compositions. More particularly, the present invention relates to photo-protective compositions that have a synergistic combination of sunscreen agent and carotenoid resulting in a SPF increase or boost to the composition, without the need for additional sunscreen agent.

2. Description of Related Art

Photo-protective compositions, such as sunscreen compositions, are applied to the skin to protect the skin from the sun's ultraviolet rays that can lead to erythema, a reddening of the skin also known as sunburn. Sunlight or ultraviolet radiation in the UV-B range has a wavelength of 290 nm to 320 nm and is known to be the primary cause of sunburn. Ultraviolet rays at a wavelength of 320 nm to 400 nm, known as UV-A radiation, produces tanning of the skin. However, in the process of doing so, the UV-A rays can damage or harm the skin.

Besides the immediate malady of sunburn, excessive sunlight exposure can lead to skin disorders. For instance, prolonged and constant exposure to the sun may lead to actinic keratoses and carcinomas. Another long-term effect is premature aging of the skin. This condition is characterized by skin that is wrinkled, cracked and has lost its elasticity.

As stated above, sunscreens are typically formulated with the goal of inhibiting skin damage from the sun's rays. The sunscreen composition filters or blocks the harmful UV-A and UV-B rays that can damage and harm the skin. It is believed that sunscreen agents accomplish this by absorbing the UV-A and/or UV-B rays. Sunscreen compositions are typically formulated with one or more sunscreen active agents, which absorb and/or block the UVA and UVB radiation. The SPF of the composition is usually controlled by the amount of sunscreen active present in the composition. Generally, the more sunscreen active included in the composition, the higher the SPF.

While compositions with sunscreen agents are effective at blocking and/or absorbing UV light, it is difficult to eliminate all of the impact of UV irradiation on the skin. Sunscreen agents alone are unable to repair the damage to the skin resulting from UV irradiation. As such, the use of carotenoids in skin care compositions to treat skin maladies that result from UV light exposure is found in the prior art. See, for example, U.S. Pat. No. 6,433,025 B1; U.S. Pat. No. 6,348,200 B1; U.S. Pat. No. 6,316,012 B1; U.S. Pat. No. 6,296,880 B1; U.S. Pat. Nos. 6,110,478; 6,071,541; and 5,712,311, all of which are incorporated by reference herein.

However, what is clearly not appreciated in the prior art, yet is unexpectedly achieved by the present invention, is a photo-protective composition having a synergistic combination of sunscreen agent and carotenoid such that a SPF increase or boost is observed in the composition as compared to a photo-protective composition without carotenoid.

SUMMARY OF THE INVENTION

It is an object of the present invention to provide a composition that has enhanced photo-protective properties achieved without the inclusion of additional sunscreen agent.

It is another object of the present invention to provide such a composition that has a synergistic combination of sunscreen agent and carotenoid.

It is still another object of the present invention to provide such a composition wherein the carotenoid in the presence of sunscreen agent synergistically increases the SPF of the composition compared to a composition without carotenoid.

To accomplish the foregoing objects and advantages, the present invention, in brief summary, is a photo-protective composition that has a synergistic combination of at least one sunscreen agent and at least one carotenoid, which results in a composition with an increased SPF over a composition without carotenoid. Preferably, the composition also has at least one of the following additional components: emulsifier, emollient, skin-feel additive, moisturizing agent, film former/waterproofing agent, pH adjuster/chelating agent, preservative, or any combinations thereof.

DETAILED DESCRIPTION OF THE INVENTION

The present invention is a photo-protective composition that includes a synergistic combination of at least one sunscreen agent and at least one carotenoid.

Contrary to conventional formulating of photo-protective compositions, which call for increasing the amount of sunscreen agent to achieve increased SPF in the composition, it has been unexpectedly found that by including a synergistically effective amount of one or more carotenoids to a composition having one or more sunscreen agents, an increase in the SPF of the composition is observed over those compositions having only sunscreen agent and no carotenoid. As a result, higher SPF can be achieved without the inclusion of additional sunscreen agent to the composition.

The fact that additional sunscreen agent is not required to boost the SPF of the composition is important in lieu of the fact that sunscreen agents that are commonly used in sunscreen compositions are regulated by the FDA. As a result of these regulations, namely the FDA Final Monograph, numerous sunscreen agents have are limited as to the maximum amount that can be included in a composition. Due to these limits, it can be difficult to formulate increased SPF compositions, since the SPF is typically related to the amount of sunscreen included in the composition. The compositions of the present invention with the one or more carotenoids overcome this problem or limitation.

The one or more sunscreen agents that can be used in the present invention must be capable of absorbing or blocking the harmful effects of ultraviolet radiation. In addition, they must be non-toxic and non-irritating when applied to the skin. Suitable sunscreen agents that may be used in the sunscreen composition include, but are not limited to, para-aminobenzoic acid (PABA), butyl methoxydibenzoylmethane (avobenzone), benzophenone-1, benzophenone-2, benzophenone-3, benzophenone4, benzophenone-6, benzophenone-8, benzophenone-12, methoxycinnamate, ethyl dihydroxypropyl-PABA, glyceryl PABA, homosalate, methyl anthranilate, octocrylene, octyl dimethyl PABA, octyl methoxycinnamate, octyl salicylate, PABA, 2-phenylbenzimidazole-5-sulphonic acid, triethanolam ine salicylate, 3-(4-methylbenzylidene)-camphor, red petrolatum, zinc oxide, titanium dioxide, 3-(4-methylbenzyldine)boran-2-one(methylbenzindinecamphor), benzotriazole, phenylbenzimidazole-5-sulfonic acid, methylene bis-benzotrizolyl tetramethylbutyl phenol, or any combinations thereof.

The preferred sunscreen agents are avobenzone, benzophenone-3, octyl methoxycinnamate, octyl salicylate, homosalate, or any combinations thereof.

The one or more sunscreen agents are included in the present composition in an amount about 1 weight percent (wt. %) to about 40 wt. %, based on the total weight of the composition. Preferably, the one or more sunscreen agents are included in an amount about 4 wt. % to about 35 wt. % to achieve a SPF of about 2 to about 50.

An important aspect of the present invention is the inclusion of one or more carotenoids in combination with the one or more sunscreen agents in the photo-protective compositions of the present invention. It has been unexpectedly found that the inclusion of small amounts of one or more carotenoids in the compositions of the present invention result in a SPF increase or boost to the composition, as compared to a composition with equal amounts of sunscreen agent and no carotenoid.

Carotenoids suitable for use in the present invention include, but are not limited to, one or more lutein, lutein esters, xanthophylls, alpha-carotene, beta-carotene, gamma-carotene, lycopene, zeaxanthin, isozeaxanthin, astaxanthin, canthaxanthin, tanaxanthin, cryptoxanthin, rhodoxanthin, capxanthin, or any combinations thereof. Preferably, the one or more carotenoids are one or more lutein, lutein esters, or any combinations thereof.

As noted above, only a small amount of carotenoid is required to be included in the compositions of the present invention to achieve the unexpected SPF boost in the composition. Carotenoid in an amount about 0.00001 wt. % to about 0.03 wt. % can be included in the composition to synergistically boost the final SPF of the composition. Preferably, the carotenoid is present in an amount about 0.00001 wt. % to about 0.02 wt. %, and more preferably in an amount about 0.00001 wt. % to about 0.011 wt. %.

The need for only a small amount of carotenoid to synergistically achieve the SPF boost with the sunscreen agent results in a cost reduction when formulating the composition and does not require significant formulation modifications to incorporate it into the composition.

In addition, it has been found that the amount of carotenoid to be used in the compositions must be carefully selected. By way of example, it has been found that the use of lutein in amounts greater than about 0.011 wt. % may color the composition excessively, which may result in the undesirable staining of the skin and fabric. In addition, it is believed that lutein at concentrations below 0.00001 wt. % does not have any biological effects on the skin.

Preferably, the composition also has one or more of the following additional components: pharmaceutically acceptable carrier, emulsifier, emollient, skin-feel additive, moisturizing agent, film former/waterproofing agent, pH adjuster/chelating agent, preservative, or any combinations thereof.

Suitable emulsifiers that may be used in the compositions of the present invention include, but are not limited to, butylated PVP, cetyl alcohol, sodium acrylate/sodium acryloyldimethyltaurate copolymer, diethylhexyl napthalate, sorbitan oleate, sorbitan sesquioleate, sorbitan isostearate, sorbitan trioleate, polyglyceryl-3-diisostearate, polyglycerol esters of oleic/isostearic acid, polyglyceryl-6 hexaricinolate, polyglyceryl-4-oleate, polyglyceryl-4 oleate/PEG-8 propylene glycol cocoate, oleamide DEA, sodium glyceryl oleate phosphate, hydrogenated vegetable glycerides phosphate, cetearyl glucoside, cocoyl glucoside, cocoyl ethyl glucoside, disodium coco-glucoside citrate, disodium coco-glucoside sulfosuccinate, lauroyl ethyl glucoside, myristoyl ethyl glucoside, octyl dimethicone ethoxy glucoside, oleoyl ethyl glucoside, sodium coco-glucoside tartrate, or any combinations thereof.

The amount of emulsifier present in the sunscreen compositions of the present invention is about 1 wt. % to about 15 wt. % of the total weight of the composition. Preferably, the emulsifier is present in an amount about 2.5 wt. % to about 7.5 wt. % of the total weight of the composition.

The compositions of the present invention also include water. Water is present in an amount about 45 wt. % to about 75 wt. %, and preferably about 50 wt. % to about 65 wt. %, of the total weight of the sunscreen composition.

The present composition may include one or more emollients. An emollient provides a softening or soothing effect on the skin surface and is generally considered safe for topical use. It also helps control the rate of evaporation and the tackiness of the sunscreen composition.

Suitable emollients include, but are not limited to, cyclomethicone, dimethicone, dicapryl maleate, caprylic/capric triglyceride, mineral oil, lanolin oil, coconut oil, cocoa butter, olive oil, aloe extracts such as aloe vera, jojoba oil, castor oil, fatty acid such as oleic and stearic, fatty alcohol such as cetyl and hexadecyl (ENJAY), diisopropyl adipate, hydroxybenzoate esters, benzoic acid esters of $C_9$-$C_{15}$ alcohols, isononyl iso-nonanoate, alkanes such as mineral oil, silicone such as dimethyl polysiloxane, ether such as polyoxypropylene butyl ether and polyoxypropylene cetyl ether, $C_{12}$-$C_{15}$ alkyl benzoate, or any combinations thereof.

The preferred emollients are cyclomethicone, dimethicone, dicapryl maleate, caprylic/capric triglyceride, aloe vera, or any combinations thereof.

The total amount of emollient present in the sunscreen composition is typically about 0.10 wt. % to about 30 wt. %, based on the total weight of the composition. The preferred amount of emollient is about 1 wt. % to about 20 wt. %.

The feel of the sunscreen composition upon application to the skin may be a consideration of a consumer when purchasing a sunscreen. Moreover, a smooth, silky sunscreen composition may be more uniformly applied over the skin. To further enhance the feel of the sunscreen compositions of the present invention when applied to the skin, a skin-feel additive may be included. Suitable skin-feel additives include, but are not limited to, synthetic polymers, silicones, esters, particulates, or any combinations thereof.

Preferably, the skin-feel additive is present in the sunscreen composition in an amount about 0.10 wt. % to about 5 wt. %, based on the total weight of the composition. More preferably, it is present in an amount about 0.30 wt. % to about 0.70 wt. % of the total weight of the composition.

The pH of the compositions of the present invention may be adjusted by one or more basic pH adjusters and/or chelating agents. For example, sodium hydroxide, triethanolamine, trisodium ethylenediaminetetraacetic acid, or any combinations thereof are suitable pH adjusters/chelating agents that may be included in the sunscreen compositions of the present invention.

An effective amount of a pH adjuster and/or chelating agent that may be included to adjust the pH of the final composition to about 3 to about 9. Preferably, the pH is adjusted to about 6 to about 8.

A moisturizing agent, such as a humectant, may be used in the compositions of the present invention. Suitable humectants include, but are not limited to, glycerin, polyethylene glycol, polypropylene glycol, pentylene glycol, caprylyl glycol, sorbitol, PEG-4, PEG-8, or any combinations thereof.

One or more moisturizing agents are optionally included in the compositions of the present invention in an amount about 0.1 wt. % to about 2 wt. % of the total weight of the composition. Preferably, about 0.25 wt. % to about 0.75 wt. % of one or more moisturizing agents may be used in the composition.

Another component that may be used in a sunscreen composition of the present invention is a film former/waterproofing agent. The film former/waterproofing agent is a hydrophobic material that imparts film forming and waterproofing characteristics to the emulsion. One such agent is polyethylene, which is available from New Phase Technologies as PERFORMALENE® 400, a polyethylene having a molecular weight of 400. Another suitable water-proofing agent is polyethylene 2000 (molecular weight of 2000), which is available from New Phase Technologies as PERFORMALENE® 2000. Yet, another suitable film former/waterproofing agent is synthetic wax, also available from New Phase Technologies as PERFORMA® V-825. One or more film formers/waterproofing agents may be present in a composition of the present invention in an amount about 0.1 wt. % to about 5 wt. %, based on the total weight of the composition.

Optionally, one or more preservatives may be included in a composition of the present invention. The preservative protects the composition from microbial contamination and/or oxidation. As such, the preservative can include an antioxidant. Preservatives, such as diazolidinyl urea, iodopropynyl butylcarbamate, chloromethylisotiazolinone, methylisothiazolinone, vitamin E and its derivatives including vitamin E acetate, vitamin C, butylated hydroxytoluene, methylparaben, or any combinations thereof, may be included as a preservative in a composition of the present invention.

About 0.01 wt. % to about 1 wt. % of preservative may be included in a composition of the present invention. Preferably, one or more preservatives total about 0.05 wt. % to about 0.50 wt. %, based on the total weight of the composition.

The sunscreen compositions of the present invention may also have other optional additives. For instance, one or more fragrances, colorants, plant extracts, absorbents, thickeners, salicylic acid, alpha and beta hydroxy acids, vitamins including vitamins A, C, and E, retinol, retinol palmitate, vitamin E acetate, tocopherol, vitamin A palmitate, vitamin E palmitate, or any mixtures thereof, may be included in the sunscreen compositions.

The components of the present invention may be combined to form a stable oil-in-water emulsion. The sunscreen is incorporated into the oil phase and later combined with water with the help of the one or more emulsifiers. The process used to manufacture the composition of the present invention must be capable of forming a homogeneous composition that can be spread into a film.

In one preferred embodiment of the present invention, the sunscreen composition includes about 12 wt. % to about 20 wt. % of one or more sunscreen agents selected from the group consisting of: octyl methoxycinnamate, octyl salicylate, butyl methoxydibenzoylmethane, benzophenone-3, or any combinations thereof; and about 0.00001 wt. % to about 0.011 wt. % of lutein.

This unexpected benefit of including one or more carotenoids in the compositions of the present invention is demonstrated in the Example below.

EXAMPLE 1

Two compositions were prepared and subsequently tested for SPF. The first composition (Composition 1) included about 16 wt. % sunscreen agents and about 0.011% lutein where the second, comparative composition (Composition 2) contained about 16 wt. % sunscreen agents and no lutein. Concurrent with the testing of the above compositions, a standard sunscreen preparation of 8% homosalate with a mean SPF value of 4.47+/−1.28 was tested. As set forth below in Table 1, overall, Composition 1 had an average measured average SPF of 31.50 where the comparative Composition 2, absent lutein, only had an average measured SPF of 29.65, demonstrating that the composition with lutein has almost 2 SPF units more than that composition without lutein.

The test procedure was based on the method outlined in the FDA Final Monograph for sunscreen testing published in the Federal Register, Vol. 64, No. 98, May 21, 1999. Further testing parameters were are follows:

Inclusion Criteria:
a) At least twenty (20) but not more than twenty-five (25) healthy male or female volunteers of skin types I-III as described below:
  I Always burns easily, never tans (sensitive)
  II Always burns easily; tans minimally (sensitive)
  III Burns moderately; tans gradually (light brown) (normal)
  IV Burns minimally; always tans well (moderate brown) (normal)
  V Rarely burns; tans profusely (dark brown) (insensitive)
  VI Never burns; deeply pigmented (insensitive)
b) Ages 18-65 years old.
c) Absence of any visible skin disease which might be confused with a skin reaction from the Test Material;
d) Completion of a Medical History Form and the understanding and signing of a legally effective Informed Consent Form; and
e) Considered dependable and capable of following directions.

Exclusion Criteria:
a) Subjects with a history of abnormal response to sunlight or those taking medication which might produce an abnormal response to sunlight;
b) Subjects exhibiting current sunburn, suntan, or uneven skin tone or visible skin disease, which might interfere with evaluation of test, results;
c) Presence of nevi, blemishes, or moles which, in the Investigator's judgement, would interfere with the study results. Excess hair on the back would be accepted if hair is clipped or shaved;
d) Subjects with a history of lupus, erythematosis, or skin cancer; and
e) Females who are pregnant or lactating.

Test Method

Seven (7) subjects who met the inclusion criteria were selected for participation.

Light Source—A Xenon Arc Solar Simulator (150 w) was used as the source of ultraviolet light irradiation (Solar Light Company, Philadelphia, P A). This instrument, described in detail in J. Invest. Dermatol. 53, 192 (1969), provides a spectral output in the ultraviolet range comparable to that of natural sunlight. The WG-320 and VG-II filters were used to provide a basic UV-A and UV-B wavelength spectrum, with wavelength ranges of 290-400 nm. The lamp output was measured with a UV intensity meter (Model PMA2100, Solar Light Company, Philadelphia, Pa.) before and after the test period.

Determination of Minimal Erythemal Dose (MED)—An MED is defined as the lowest time interval or dosage of UV light irradiation sufficient to produce defined erythema on designated test sites. Prior to the product testing phase, the MED of the unprotected skin of each subject was determined by a progressive sequence of timed UV light exposures, graduated incrementally by 25% over that of the previous exposure. The sites were evaluated for erythema according to the following scoring system:

| | |
|---|---|
| 0 | No reaction |
| 0.5 | Equivocal reaction, barely perceptible erythema with no clearly defined border |
| 1 | Mild but definite erythema with clearly defined border |
| 2 | Moderate clearly defined erythema |
| 3 | Strong erythema, edema |
| 4 | Bulla or vesiculation |

Determination of Static SPF Values—A sufficient number of 50 square centimeter test site areas were outlined with a surgical marking pen on the subject's back between the scapulae and the beltline, lateral to the midline. These areas were designated for applications of the Test Material and Standard, with an adjacent site designated for a concurrent MED determination (unprotected control).

A 2 mg/cm² portion of the Test Material and of the Standard was applied to the appropriate designated test site and spread evenly over the site using a fingercot. After product application, each test area was subdivided into sites, which were used for defined serial UV light exposures. Irradiation of the sites was begun no less than 15 minutes after application.

Exposure times were selected for each site in treated areas based upon the previously determined MED of unprotected skin and the expected SPF of the Test Material and the HMS Standard. After irradiation was completed for each area, responses for tanning, reddening, and heat response were recorded as absent (O) or present (1).

Evaluation of Test Sites—All test sites were evaluated 22 to 24 hours after irradiation to determine minimal erythemal response of all sites. The MED evaluator did not apply or irradiate the test material.

SPF Determination—The SPF is defined as the ratio of the amount of energy or time required to produce an MED on protected skin (treated with Test Material(s) or Standard) to the amount of energy or time needed to produce an MED on untreated skin and is calculated as follows:

$$SPF = \frac{MED \text{ Test Material or Standard}}{MED \text{ Unprotected Control}}$$

TABLE 1

| | 8% Homosalate Standard | Composition 1 | Composition 2 |
|---|---|---|---|
| Average SPF Value | 4.70 | 31.50 | 29.65 |

Again, as demonstrated by the data summarized in Table 1, Composition 1, which included lutein according to the present invention had a SPF value almost 2 SPF units higher than Composition 2, which did not include lutein. Therefore, an SPF boost is observed without the inclusion of additional sunscreen agent.

The sunscreen compositions of the present invention may be prepared by using techniques and methods well known in the art. In general, ingredients are incorporated by mixing and applying heat if necessary, until the composition is uniform and homogeneous. The composition may be homogenized to ensure homogeneity and to build the proper viscosity. The sunscreen compositions of the present invention are then packaged as a lotion in any package or container suitable for a sunscreen composition.

Having thus described the present invention with particular reference to preferred embodiments thereof, it will be apparent that various changes and modifications may be made therein without departing from the spirit and scope of the present invention as defined in the appended claims.

What is claimed is:

1. A photo-protective composition consisting of:
    at least one sunscreen agent present in an amount of about 4 wt. % to about 35 wt. %, based on the total weight of said composition, and selected from the group consisting of para-aminobenzoic acid (PABA), butyl methoxydibenzoylmethane (avobenzone), benzophenone-1, benzophenone-2, benzophenone-3, benzophenone-4, benzophenone-6, benzophenone-8, benzophenone-12, methoxycinnamate, ethyl dihydroxypropyl-PABA, glyceryl PABA, homosalate, methyl anthranilate, octocrylene, octyl dimethyl PABA, octyl methoxycinnamate, octyl salicylate, 2-phenylbenzimidazole-5-sulphonic acid, triethanolamine salicylate, 3-(4-methylbenzylidene)-camphor, red petrolatum, zinc oxide, titanium dioxide, 3-(4-methylbenzyldine)boran-2-one(methylbenzindinecamphor), benzotriazole, phenylbenzimidazole-5-sulfonic acid, methylene bis-benzotrizolyl tetramethylbutyl phenol, and any combinations thereof;
    at least one carotenoid present in an amount of about 0.00001 wt. % to about 0.011 wt. %, and selected from the group consisting of lutein, lutein ester, xanthophyll, alpha-carotene, beta-carotene, gamma-carotene, lycopene, zeaxanthin, isozeaxanthin, astaxanthin, canthaxanthin, tanaxanthin, cryptoxanthin, rhodoxanthin, capxanthin, and any combinations thereof;
    water; and
    optionally, at least one component selected from the group consisting of:
        an emulsifier selected from the group consisting of butylated polyvinyl pyrrolidone, cetyl alcohol, sodium acrylate/sodium acryloyldimethyltaurate copolymer, diethylhexyl naphthalate, sorbitan oleate, sorbitan sesquioleate, sorbitan isostearate, sorbitan trioleate, polyglyceryl-3-diisostearate, polyglycerol esters of oleic/isostearic acid, polyglyceryl-6 hexaricinolate, polyglyceryl-4-oleate, polyglyceryl-4 oleate/PEG-8 propylene glycol cocoate, oleamide diethanolamine, sodium glyceryl oleate phosphate, hydrogenated vegetable glycerides phosphate, cetearyl glucoside, cocoyl glucoside, cocoyl ethyl glucoside, disodium coco-glucoside citrate, disodium coco-glucoside sulfosuccinate, lauroyl ethyl glucoside, myristoyl ethyl glucoside, octyl dimethicone ethoxy glucoside, oleoyl ethyl glucoside, sodium coco-glucoside tartrate, and any combinations thereof;
        an emollient selected from the group consisting of cyclomethicone, dimethicone, dicapryl maleate, caprylic/capric triglyceride, mineral oil, lanolin oil, coconut oil, cocoa butter, olive oil, aloe extracts, jojoba oil, castor oil, fatty acid, fatty alcohol, diisopropyl adipate, hydroxybenzoate esters, benzoic acid esters of C9-C15 alcohols, isononyl iso-nonanoate, alkanes, silicones, ethers, C12-C15 alkyl benzoate, and any combinations thereof;
        a skin-feel additive selected from the group consisting of synthetic polymers, silicones, esters, particulates, and any combinations thereof;
        a moisturizing agent selected from the group consisting of glycerin, polyethylene glycol, polypropylene glycol, pentylene glycol, caprylyl glycol, sorbitol, PEG-4, PEG-8, and any combinations thereof;

a film former/waterproofing agent selected from the group consisting of polyethylene 400, polyethylene 2000, and synthetic wax;

a pH adjuster/chelating agent selected from the group consisting of sodium hydroxide, triethanolamine, trisodium ethylenediaminetetraacetic acid, and any combinations thereof; and a preservative selected from the group consisting of diazolidinyl urea, iodopropynyl butylcarbamate, chloromethylisotiazolinone, methylisothiazolinone, vitamin E, vitamin E acetate, vitamin C, butylated hydroxytoluene, methylparaben, and any combinations thereof, wherein said at least one sunscreen agent and said at least one carotenoid provide a synergistic combination that results in said photo-protective composition having a higher SPF than a photo-protective composition without said synergistic combination, and wherein said composition has a pH of from about 6 to about 8.

2. The photo-protective composition according to claim 1, wherein said at least one sunscreen agent is selected from the group consisting of avobenzone, benzophenone-3, octyl methoxycinnamate, octyl salicylate, homosalate, and any combinations thereof.

3. The photo-protective composition according to claim 1, wherein said photo-protective composition has a SPF of about 2 to about 50.

4. The photo-protective composition according to claim 1, wherein said at least one carotenoid is selected from the group consisting of lutein, lutein ester, and any combinations thereof.

5. The photo-protective composition of claim 1, wherein said composition is an oil-in-water emulsion.

6. A photo-protective composition consisting of:
at least one sunscreen agent present in an amount of about 12 wt. % to about 20 wt. %, based on a total weight of said composition, and selected from the group consisting of butyl methoxydibenzoylmethane (avobenzone), benzophenone-3, octyl methoxycinnamate, octyl salicylate, and any combinations thereof;

lutein, present in an amount of about 0.00001 wt. % to about 0.011 wt. %, based on a total weight of said composition;

water; and optionally, at least one component selected from the group consisting of:
an emulsifier selected from the group consisting of butylated polyvinyl pyrrolidone, cetyl alcohol, sodium acrylate/sodium acryloyldimethyltaurate copolymer, diethylhexyl naphthalate, sorbitan oleate, sorbitan sesquioleate, sorbitan isostearate, sorbitan trioleate, polyglyceryl-3-diisostearate, polyglycerol esters of oleic/isostearic acid, polyglyceryl-6 hexaricinolate, polyglyceryl-4-oleate, polyglyceryl-4 oleate/PEG-8 propylene glycol cocoate, oleamide diethanolamine, sodium glyceryl oleate phosphate, hydrogenated vegetable glycerides phosphate, cetearyl glucoside, cocoyl glucoside, cocoyl ethyl glucoside, disodium coco-glucoside citrate, disodium coco-glucoside sulfosuccinate, lauroyl ethyl glucoside, myristoyl ethyl glucoside, octyl dimethicone ethoxy glucoside, oleoyl ethyl glucoside, sodium coco-glucoside tartrate, and any combinations thereof;

an emollient selected from the group consisting of cyclomethicone, dimethicone, dicapryl maleate, caprylic/capric triglyceride, mineral oil, lanolin oil, coconut oil, cocoa butter, olive oil, aloe extracts, jojoba oil, castor oil, fatty acid, fatty alcohol, diisopropyl adipate, hydroxybenzoate esters, benzoic acid esters of C9-C15 alcohols, isononyl iso-nonanoate, alkanes, silicones, ethers, C12-C15 alkyl benzoate, and any combinations thereof;

a skin-feel additive selected from the group consisting of synthetic polymers, silicones, esters, particulates, and any combinations thereof;

a moisturizing agent selected from the group consisting of glycerin, polyethylene glycol, polypropylene glycol, pentylene glycol, caprylyl glycol, sorbitol, PEG-4, PEG-8, and any combinations thereof;

a film former/waterproofing agent selected from the group consisting of polyethylene 400, polyethylene 2000, and synthetic wax;

a pH adjuster/chelating agent selected from the group consisting of sodium hydroxide, triethanolamine, trisodium ethylenediaminetetraacetic acid, and any combinations thereof; and a preservative selected from the group consisting of diazolidinyl urea, iodopropynyl butylcarbamate, chloromethylisotiazolinone, methylisothiazolinone, vitamin E, vitamin E acetate, vitamin C, butylated hydroxytoluene, methylparaben, and any combinations thereof, wherein said at least one sunscreen agent and said lutein provide a synergistic combination that results in said photo-protective composition having a higher SPF than a photo-protective composition without said synergistic combination.

7. A method for enhancing a SPF of a photo-protective composition comprising the step of incorporating at least one sunscreen agent and at least one carotenoid in said photo-protective composition, wherein said at least one sunscreen agent is present in an amount about 12 wt. % to about 25 wt. %, based on the total weight of said composition, and selected from the group consisting of avobenzone, benzophenone-3, octyl methoxycinnamate, octyl salicylate, homosalate, and any combinations thereof, and wherein said at least one carotenoid is present in an amount about 0.00001 wt. % to about 0.011 wt. %, based on the total weight of said composition, and selected from the group consisting of lutein, lutein ester, and any combinations thereof, wherein said at least one sunscreen agent and said at least one carotenoid provide a synergistic combination that results in said photo-protective composition having a higher SPF than a photo-protective composition without said synergistic combination, and wherein said photo-protective composition consists of:
said synergistic combination of at least one sunscreen agent and at least one carotenoid;

water; and optionally, at least one component selected from the group consisting of:
an emulsifier selected from the group consisting of butylated polyvinyl pyrrolidone, cetyl alcohol, sodium acrylate/sodium acryloyldimethyltaurate copolymer, diethylhexyl naphthalate, sorbitan oleate, sorbitan sesquioleate, sorbitan isostearate, sorbitan trioleate, polyglyceryl-3-diisostearate, polyglycerol esters of oleic/isostearic acid, polyglyceryl-6 hexaricinolate, polyglyceryl-4-oleate, polyglyceryl-4 oleate/PEG-8 propylene glycol cocoate, oleamide diethanolamine, sodium glyceryl oleate phosphate, hydrogenated vegetable glycerides phosphate, cetearyl glucoside, cocoyl glucoside, cocoyl ethyl glucoside, disodium coco-glucoside citrate, disodium coco-glucoside sulfosuccinate, lauroyl ethyl glucoside, myristoyl ethyl glucoside, octyl dimethicone ethoxy glucoside, oleoyl ethyl glucoside, sodium coco-glucoside tartrate, and any combinations thereof;

an emollient selected from the group consisting of cyclomethicone, dimethicone, dicapryl maleate, caprylic/capric triglyceride, mineral oil, lanolin oil, coconut oil, cocoa butter, olive oil, aloe extracts, jojoba oil, castor oil, fatty acid, fatty alcohol, diisopropyl adipate, hydroxybenzoate esters, benzoic acid esters of C9C15 alcohols, isononyl iso-nonanoate, alkanes, silicones, ethers, C12C15 alkyl benzoate, and any combinations thereof;

a skin-feel additive selected from the group consisting of synthetic polymers, silicones, esters, particulates, and any combinations thereof;

a moisturizing agent selected from the group consisting of glycerin, polyethylene glycol, polypropylene glycol, pentylene glycol, caprylyl glycol, sorbitol, PEG-4, PEG-8, and any combinations thereof;

a film former/waterproofing agent selected from the group consisting of polyethylene 400, polyethylene 2000, and synthetic wax;

a pH adjuster/chelating agent selected from the group consisting of sodium hydroxide, triethanolamine, trisodium ethylenediaminetetraacetic acid, and any combinations thereof; and a preservative selected from the group consisting of diazolidinyl urea, iodopropynyl butylcarbamate, chloromethylisotiazolinone, methylisothiazolinone, vitamin E, vitamin E acetate, vitamin C, butylated hydroxytoluene, methylparaben, and any combinations thereof.

8. The method of claim 7, wherein said photo-protective composition has a pH of from about 6 to about 8.

9. The photoprotective composition of claim 1, wherein said pH adjuster/chelating agent is present in the photoprotective composition.

10. The photoprotective composition of claim 1, wherein said preservative is present in an amount of about 0.01 wt % to about 1 wt %, based on the total weight of the composition.

11. The photoprotective composition of claim 1, wherein said emulsifier is present in an amount of about 1 wt % to about 15 wt %, based on the total weight of the composition.

12. The photoprotective composition of claim 1, wherein said emollient is present in an amount of about 0.10 wt % to about 30 wt %, based on the total weight of the composition.

* * * * *